United States Patent [19]

King

[11] Patent Number: 4,584,317

[45] Date of Patent: Apr. 22, 1986

[54] PESTICIDAL TIN AMIDOXIMES

[75] Inventor: William F. King, Novato, Calif.

[73] Assignee: Chevron Research Company, San Francisco, Calif.

[21] Appl. No.: 649,459

[22] Filed: Sep. 11, 1984

[51] Int. Cl.$^4$ .................. A01N 55/04; C07F 7/28; A61K 31/32

[52] U.S. Cl. ..................... 514/493; 556/37; 71/97

[58] Field of Search .............. 260/429.7; 71/97; 514/493; 556/37

[56] References Cited

U.S. PATENT DOCUMENTS

| | | | |
|---|---|---|---|
| 2,988,534 | 6/1961 | Eckelmann | 260/429.7 X |
| 3,275,659 | 9/1966 | Weissenberger | 260/429.7 X |
| 3,480,653 | 11/1969 | Pandi | 260/429.7 X |
| 3,565,860 | 2/1971 | Pandi | 260/429.7 X |
| 4,294,772 | 10/1981 | Martin | 260/429.7 |
| 4,400,527 | 8/1983 | Mathew et al. | 260/429.7 X |
| 4,478,756 | 10/1984 | Martin | 260/429.7 |

Primary Examiner—Helen M. S. Sneed

Attorney, Agent, or Firm—S. R. LaPaglia; T. G. DeJonghe; S. L. Biggs

[57] ABSTRACT

Compounds of the formula:

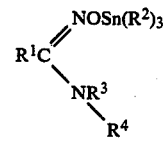

wherein $R^1$ is lower alkyl of 1 to 6 carbon atoms; alkylthioalkylene of 2 to 5 carbon atoms; aryl of 6 to 10 carbon atoms; aralkyl of 7 to 12 carbon atoms; arylthioalkyl of 7 to 11 carbon atoms; or substituted aryl, substituted aralkyl or substituted arylthioalkyl each substituted with 1 to 3 substituents independently selected from halo, nitro, lower alkoxy of 1 to 4 carbon atoms, or lower alkyl of 1 to 4 carbon atoms; $R^2$ is lower alkyl of 1 to 6 carbon atoms, lower cycloalkyl of 3 to 8 carbon atoms, phenyl or benzyl; and $R^3$ and $R^4$ are independently hydrogen, lower alkyl of 1 to 6 carbon atoms or phenyl, are pesticidal.

28 Claims, No Drawings

PESTICIDAL TIN AMIDOXIMES

BACKGROUND OF THE INVENTION

The present invention relates to pesticidal tin amidoxime compounds. The compounds of my invention are useful in protecting plants against a variety of pests.

Certain amidoximes have been disclosed as exhibiting herbicidal and phytohormonal activity. See e.g., U.S. Pat. Nos. 4,116,974; 4,216,006; and 4,324,579.

Various organo-tin compounds have been disclosed as having biocidal activities. See, e.g., U.S. Pat. Nos. 3,657,451; 3,906,103; 3,987,191; and 4,224,338.

SUMMARY OF THE INVENTION

The pesticidal tin amidoxime compounds of my invention are represented by the general formula:

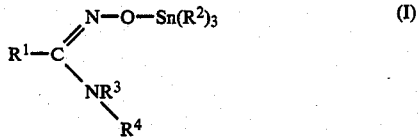

wherein $R^1$ is lower alkyl of 1 to 6 carbon atoms; alkylthioalkylene of 2 to 5 carbon atoms; aryl of 6 to 10 carbon atoms; aralkyl of 7 to 12 carbon atoms; arylthioalkyl of 7 to 11 carbon atoms; or substituted aryl, substituted aralkyl or substituted arylthioalkyl each substituted with 1 to 3 substituents independently selected from halo, nitro, lower alkoxy of 1 to 4 carbon atoms, or loweer alkyl of 1 to 4 carbon atoms; $R^2$ is lower alkyl of 1 to 6 carbon atoms, lower cycloalkyl of 3 to 8 carbon atoms, phenyl, or benzyl; and $R^3$ and $R^4$ are independently hydrogen, lower alkyl of 1 to 6 carbon atoms, or phenyl.

Among other factors, the present invention is based on my surprising finding that these compounds are effective in controlling a wide variety of pests including certain plant fungal diseases.

Preferred compounds include those where $R^1$ is alkylthioalkylene, aryl, substituted aryl, and the like.

Preferred $R^1$ groups include methylthiomethylene, phenyl, p-fluorophenyl, p-bromophenyl, o-chlorophenyl, p-chlorobenzyl, 2,4-dichlorophenylthiomethylene, phenylthiomethylene, n-propylthiomethylene, isopropylthiomethylene, and the like.

Preferred $R^2$ groups include n-butyl, cyclohexyl, phenyl, benzyl, and the like.

Preferred $R^3$ groups include hydrogen, methyl, ethyl, isopropyl, phenyl, and the like.

Especially preferred $R^1$ groups include methylthiomethylene, n-propylthiomethylene, isopropylthiomethylene, phenylthiomethylene, and the like.

Especially preferred $R^2$ groups include n-butyl, cyclohexyl, and the like.

Especially preferred $R^3$ groups include hydrogen.

Representative compounds of this invention are included in Table I.

DEFINITIONS

As used herein, the following terms have the following meanings unless expressly stated to the contrary.

The term "alkyl" refers to both straight- and branched-chain alkyl groups. The term "lower alkyl" refers to both straight- and branched-chain alkyl groups having a total of from 1 to b 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "cycloalkyl" refers to cyclic alkyl groups. The term "lower cycloalkyl" refers to groups having from 3 to 6 carbon atoms in the ring, and includes cyclopropyl, cyclobutyl, cyclopentyl, and cyclohexyl.

The term "alkylene" refers to the group —$(CH_2)_m$— wherein m is an integer greater than zero. Typical alkylene groups include, methylene, ethylene, propylene and the like.

The term "alkylthio" refers to the group R'S— wherein R' is alkyl. The term "lower alkylthio" refers to alkylthio groups having 1 to 6 carbon atoms; examples include methylthio, ethylthio, n-hexylthio, and the like.

The term "alkylthioalkylene" refers to an alkyl group substituted with an alkylthio group. The term "lower alkylthioalkylene" refers to groups having up to a total of 8 carbon atoms and includes, for example, ethylthiomethylene, methylthiomethylene, 2-methylthiopropylene, and the like.

The term "alkoxy" refers to the group —OR' wherein R' is an alkyl group. The term "lower alkoxy" refers to alkoxy groups having from 1 to 6 carbon atoms; examples include methoxy, ethoxy, n-hexoxy, n-propoxy, isopropoxy, isobutoxy, and the like.

The term "alkoxyalkylene" refers to an alkyl group substituted with an alkoxy group. The term "lower alkoxyalkylene" refers to groups having up to a total of 8 carbon atoms and includes, for example, ethoxymethylene, methoxymethylene, 2-methoxypropylene, and the like.

The term "alkenyl" refers to unsaturated alkyl groups having a double bond [e.g., $CH_3CH=CH(CH_2)_2$] and includes both straight- and branched-chain alkenyl groups. "Lower alkenyl" refers to groups having a total of from 3 to 6 carbon atoms. Typical lower alkenyl groups include, for example, propenyl, but-3-enyl, hex-4-enyl, 2-methylpent-4-enyl, and the like.

The term "halo" or "halogen" refers to the groups fluoro, chloro, bromo and iodo.

The term "haloalkenyl" refers to alkenyl groups substituted with from 1 to 2 halogen atoms. "Lower haloalkenyl" refers to groups having a total of from 3 to 5 carbom atoms, and includes, for example, 1-chloropropenyl, 2,3-dibromo-but-3-enyl, and the like.

The term "alkynyl" refers to unsaturated alkyl groups having a triple bond (e.g., $CH_3C \equiv CCH_2CH_3$) and includes both straight- and branched-chain alkynyl groups. "Lower alkynyl" refers to groups having a total of from 3 to 5 carbon atoms. Typical lower alkynyl groups include propynyl, butynyl, and the like.

The term "hydroxy alkyl" refers to the group —R'-'OH wherein R" is branched or unbranched alkylene and the hydroxy can be on a primary, secondary or a tertiary carbon. Examples include hydroxy ethyl and 2-hydroxypropyl and 2-hydroxy-2-methyl butyl.

The term "aryl" refers to aryl groups having from 6 to 10 carbon atoms and includes, for example, phenyl, p-chlorophenyl, m-methylphenyl, p-butylphenyl, m-trifluoromethylphenyl, naphthyl, and the like.

The term "aralkyl" refers to an alkyl group of 1 to 4 carbons substituted with an aryl group of from 6 to 10 carbons and includes, for example, benzyl, p-chlorobenzyl, p-methylbenzyl and 2-phenylethyl.

The term "arylthio" refers to the group R'''S— wherein R''' is an aryl group; examples include phenylthio, naphthylthio, and the like.

The term "arylthioalkyl" refers to an alkyl group of 1 to 4 carbon atoms substituted with an arylthio group and includes, for example, phenylthiomethylene, naphthylthiomethylene, phenylthioethylene, and the like.

The term "alkylamino" refers to the group R'R"N— wherein R' is alkyl and R" is hydrogen or alkyl. The term "lower alkylamino" refers to alkylamino groups having 1 to 6 carbon atoms. Typical alkylamino groups include methylamino, ethylamino, diethylamino, dimethylamino, and the like.

Pests are any insect, rodent, nematode, fungus, weed, or any form of terrestrial or aquatic plant or animal life or virus, bacterial organism or other microorganism (except those viruses, bacteria or other microorganisms existing in living humans or other living animals) considered injurious to health, the environment or man's economic well-being.

Pesticides are chemical entities or mixtures thereof intended for preventing, destroying, repelling or mitigating any pest.

The term "pesticide", when not specifically modified or delimited by other words, sometimes includes any one or a combination of the following: the active ingredient, the pesticide formulation or the pesticide product. It may also include baits for attracting and ultimately killing amphibian and reptile pests.

The terms "insecticide" and "insect" as used herein refer to their broad and commonly understood usages rather than to those creatures which, in the strict biological sense, are classified as insects. Thus, the term "insect" is used not only to include small invertebrate animals belonging to the class "Insecta", but also to other related classes of arthropods, whose members are segmented invertebrates having more or fewer than six legs such as spiders, mites, ticks, centipedes, worms, and the like.

Miticides prevent, inhibit or destroy any of the acarine arachnid arthropods (except ticks) which are common pests to cotton, pecans, mushrooms, avocados, wheat, apples, chickens and other life forms.

Nematocides prevent, repel, inhibit or destroy any members of the class Nematoda. These animals, often called threadworms, roundworms and eelworms, are injurious to plants. They feed on roots, stems, leaves or flowers.

DETAILED DESCRIPTION OF THE INVENTION

The compounds of the present invention may be conveniently prepared according to the following reaction scheme:

(a) where $R^3$ and $R^4$ are both hydrogen:

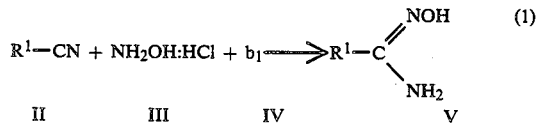
(1)

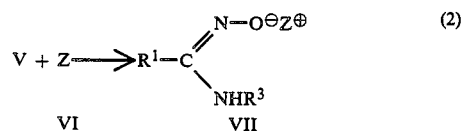
(2)

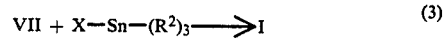
(3)

wherein $R^1$ and $R^2$ are as previously defined in conjunction with formula I, $b_1$ is a base, Z is a basically reacting metal compound which is capable of removing the proton from the oxime of V, and X is halogen.

Reaction (1) is conducted by combining II, III and IV in solvent. It is preferred to slowly add II to a mixture of III and IV in solvent to obtain better yields. Intermediate II is prepared by well-characterized methods known to those skilled in the art or alternatively may be commercially available. Although approximately equimolar amounts of II, III and IV may be used, it is preferred to use a slight excess of III and IV (in relation to II), on the order of about 1.05 to 1.1 equivalents III and about 1.05 to about 1.1 equivalents IV per equivalent II. Suitable solvents include solvents such as ethanol, methanol, ethanol-water (90%), water, and the like.

Reaction (2) is conducted by combining approximately equimolar amounts of V and VI in solvent. It is preferred to add VI to V in solvent. Suitable basically reacting metal compounds include alkali (Group IA) metals such as sodium and potassium, sodium hydride, butyllithium, and the like. Suitable solvents include such as methanol, ethanol, dimethoxyethane, and the like. The reaction is conducted at a temperature of about 0° C. to about 20° C., preferably from about 10° C. to about 20° C. or for convenience at ambient temperature, and is generally complete within about 4 to about 24 hours. The product, VII, is isolated by conventional procedures such as stripping under reduced pressure, crystallization, filtration, and the like. Alternatively, after stripping of the solvent, product VII may be used directly in Reaction (3) without further isolation.

Reaction (3) is conducted by combining approximately equimolar amounts of VII and VIII in solvent. It is preferred to add VIII to VII in solvent. Suitable solvents include organic solvents such as dimethoxyethane, tetrahydrofuran, low molecular weight dialkyl ethers, and the like. The reaction is conducted at a temperature of about 20° C. to about 80° C., or at reflux and is generally complete within about 4 to about 24 hours. The product, I, is isolated by conventional procedures such as stripping, extraction, washing, filtration, and the like.

(b) Where $R^3$ and $R^4$ are not both hydrogen:

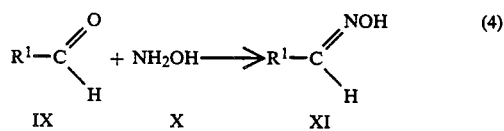
(4)

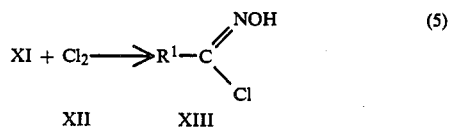
(5)

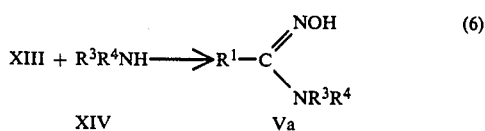
(6)

wherein $R^1$, $R^3$, and $R^4$ are as previously defined in conjunction with formula I.

Reaction (4) is conducted by combining IX and X in solvent. Although approximately equimolar amounts of IX and X may be used, it is preferred to use a slight excess of X relative to IX, on the order of up to about 1.2 equivalents X per equivalent IX. Suitable solvents include low molecular weight alcohols such as ethanol, methanol, and the like. Hydroxylamine, X, may be conveniently prepared in situ by using an hydroxylamine salt such as the hydrochloride and a strong inorganic base in the ratio of about equivalent base per equivalent hydroxylamine salt. Suitable bases include strong inorganic bases such as sodium hydroxide, potassium hydroxide, potassium carbonate, sodium carbonate, and the like. The reaction is conducted at a temperature of about 20° C. to about 80° C. or at reflux, and is generally complete within about 4 to 8 hours. The product, XI, is isolated by conventional procedures such as filtration, stripping, washing, and the like.

Reaction (5) is conducted by combining XI and XII in solvent, preferably by bubbling chlorine gas, XII, into a stirred mixture of XI in solvent. Suitable solvents include inert organic solvents such as carbon tetrachloride, chloroform, ether, methylene chloride, and the like. The reaction is conducted at a temperature of about −10° C. to about 0° C., and is generally complete within about 8 to about 12 hours. The product, XIII, is isolated by conventional procedures such as stripping, and the like.

Reaction (6) is conducted by combining XIII and XIV in solvent. It is preferred to slowly add XIV to a mixture of XIII in solvent. Suitable solvents include inert organic solvents such as methylene chloride, chloroform, ether, benzene, tetrahydrofuran, and the like. Approximately two equivalents XIV per equivalent XIII are used, with the excess XIV acting as a scavenger for chloride ions. Alternatively, approximately equivalent amounts of XIII and XIV may be used with the addition of one equivalent of a tertiary base such as triethylamine, pyridine, or the like, per equivalent XIII as the chloride scavenger. The reaction is conducted at a temperature of about 10° C. to about 80° C. or at reflux, and is generally complete within about 4 to about 8 hours. Preferably, the reaction mixture is cooled to a temperature of about 0° C. to about 10° C. during the addition, is allowed to come to room temperature, and then refluxed. The product, Va, is isolated by conventional procedures such as stripping, extraction, washing, filtration, and the like.

Intermediate Va is then converted to the compounds of this invention as outlined in Reactions (2) and (3).

UTILITY

The compounds of the present invention are useful in controlling a wide variety of pests.

These compounds are active as fungicides and are particularly effective in controlling a variety fungi which are deleterious to plants, including plant fungal infections. These compounds are particularly effective in controlling leaf blights caused by organisms such as *Phytophthora infestans* and *Septoria apii*. In addition, some of these compounds are useful in controlling early blights caused by organisms such as *Alternaria solani*, downy mildews such as that caused by *Plasmopara viticola*, and powdery mildew such as that caused by *Erisiphe polygoni*. However, some of the compounds of this invention may be more fungicidally active than others against particular fungi.

In addition, some of the compounds of this invention show antibacterial activity and may inhibit bacterial growth.

These compounds are also effective as insecticides and acaracides and may be used in controlling a variety of insect and arthropod pests. In particular, these compounds are especially effective as miticides. However, some of these compounds may be more insecticidally and acaricidally active than others against particular pests.

Like most insecticides, they are not usually applied full strength, but are generally incorporated with conventional biologically inert extenders or carriers normally employed for facilitating dispersion of active ingredients for agricultural chemical application, recognizing the accepted fact that the formulation and mode of application may affect the activity of a material. The toxicants of this invention may be applied as sprays, dusts, or granules to the insects, their environment or hostages susceptible to insect attack. They may be formulated as granules of large particle size, powdery dusts, wettable powders, emulsifiable concentrates, solutions, or as any of several other known types of formulations, depending on the desired mode of application.

Wettable powders are in the form of finely divided particles which disperse readily in water or other dispersants. These compositions normally contain from about 5% to 80% insecticide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alochols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the insecticidal composition.

Dusts are freely flowing admixtures of the active insecticide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the insecticide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for insecticidal applications include simple solutions of the active insecticide in a dispersant in which it is completely soluble at the desired concentration, such as acetone, alkylated naphthalenes, xylene, or other organic solvents. Granular formulations, wherein the insecticide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying insecticides are well known in the art.

The percentages by weight of the insecticide may vary according to the manner in which the composition is to be applied and the particular type of formulation, but in general comprise 0.5% to 95% of the toxicant by weight of the insecticidal composition.

The insecticidal compositions may be formulated and applied with other active ingredients, including nematocides, insecticides, fungicides, bactericides, plant-growth regulators, fertilizers, etc. In applying the chemical, an effective amount and concentration of the toxicant of this invention is, of course, employed.

The terms "insecticide" and "insect" as used herein refer to their broad and commonly understood usage rather than to those creatures which, in the strict biological sense, are classified as insects. Thus, the term "insect" is used not only to include small invertebrate animals belonging to the class "Insecta", but also to other related classes of arthropods, whose members are segmented invertebrates having more or fewer than six legs, such as spiders, mites, ticks, centipedes, worms, and the like.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperature ranges refer to the Centigrade system and the term "ambient" or "room temperature" refers to about 20° C. to about 25° C. The term "percent" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

EXAMPLES

Example 1

Preparation of Methylthioacetoamidoxime

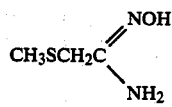

To a mixture of 21.9 g (0.315 mole) hydroxylamine hydrochloride and 33.5 g (0.316 mole) sodium carbonate in about 400 ml ethanol which had been stirred for about 15 minutes, 25 g (0.287 mole) (methylthio)acetonitrile in a small amount of ethanol was added dropwise over about 20 minutes. The reaction mixture was then stirred about ½ hour and then refluxed for about 6 hours. The reaction mixture was allowed to cool; ethyl ether (about 100 ml) was added. The mixture was stirred ½ hour and then filtered. The precipitate was washed with acetone-ethyl ether. The washings and filtrate were combined and stripped to give an oil. The oil was crystallized by trituration with ethyl ether-hexane to give 29.3 g of the above-identified product as a semi-solid.

Elemental analysis for $C_3H_8N_2OS$ showed: calculated %C 29.98, %H 6.71, and %N 23.31; found %C 31.03, %H 6.89, and %N 24.64.

Example 2

Preparation of (O-Tri-n-butylstannyl)methylthioacetamidoxime-ether

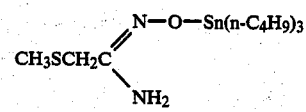

(a) To a stirred mixture of 3.8 g (0.031 moles) methylthioacetoamidoxime (the product of Example 1) in methanol (about 50 ml), 0.7 g (0.031 moles) sodium metal were added slowly until completely dissolved. The methanol was stripped under reduced pressure and heat to give the product as the sodium salt which was used in step (b) without further isolation.

(b) Dimethoxy ethane (about 75 ml) was added to the sodium salt from step (a). To the resulting mixture, 5.9 g (0.03 moles) tributyl tin fluoride was added. The reaction mixture was refluxed for 20 hours. The dimethoxyethane was stripped under reduced pressure and heat; methylene chloride (about 75 ml) and water (about 50 ml) were added to the residue and the resulting mixture was stirred about 30 minutes. The layers were phase separated. The methylene chloride phase was washed with water. The methylene chloride phase was dried with magnesium sulfate, filtered and stripped to give the above-identified product, as a light yellow liquid.

Elemental analysis for $C_{15}H_{34}N_2OSSn$ showed: calculated %C 44.0; %H 8.38; and %N 6.85; found %C 47.56; %H 9.0, and %N 4.0.

Example 3

Preparation of p-Chlorobenzylamidoxime

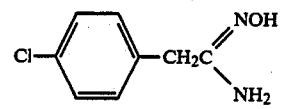

To a stirred mixture of 100 g (0.66 moles) p-chlorobenzyl cyanide and 85 g (0.8 moles) sodium carbonate in ethanol (about 300 ml), 55 g (0.79 moles) hydroxylamine hydrochloride were added. The reaction mixture was then heated to reflux and refluxed for about seven hours. The reaction mixture was cooled to room temperature and then suction-filtered. The filtrate was stripped under reduced pressure and heat to give a thick oil. Acetone (about 150 ml) was added to the oily residue. The acetone solution was filtered to remove salts. The solvent was stripped to give 121.6 g of the above-identified product as an off-white solid.

Elemental analysis for $C_8H_9ClN_2O$ showed: calculated %C 52.0, %H 4.91, and %N 15.2; found %C 51.71, %H 5.09, and %N 14.91.

Example 4

Preparation of O-Tri-n-butylstannyl-p-chlorobenzylamidoxime-ether

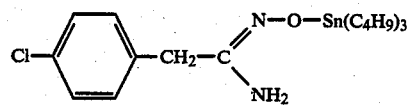

P-Chlorobenzylamidoxime sodium salt, 5 g (0.024 mole), and tri-n-butyl tin fluoride, 4.8 g (0.024 moles) were combined in methanol (about 75 ml) at room temperature. The reaction mixture was then heated to reflux and the temperature maintained at reflux overnight. The reaction mixture was allowed to reflux an additional four hours. The methanol was removed under reduced pressure and heat. Water (about 75 ml) and methylene chloride (about 125 ml) were added to the residue and the resulting mixture was stirred. The layers were phase separated. The methylene chloride phase was washed with water. Then charcoal and celite were added; the resulting mixture was stirred, filtered, and stripped to give 6.1 g of the above-identified product as an amber liquid.

Elemental analysis for $C_{20}H_{35}ClN_2OSn$ showed: calculated %C 50.7, %H 7.5, and %N 5.91; found %C 51.47, %H 7.6, and %N 6.62.

Example 5

Preparation of 2-Chlorobenzamidoxime

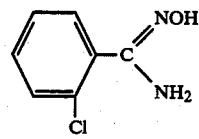

A mixture of 32 g (0.46 moles) hydroxylamine hydrochloride and 49 g (0.46 moles) sodium carbonate in ethanol (about 200 ml) was stirred at room temperature for several minutes; then, 52.4 g (0.381 moles) chlorobenzonitrile was added slowly. The reaction mixture was heated to reflux and allowed to reflux about 6 hours. The reaction mixture was cooled at room temperature and suction-filtered. The solids were washed with acetone. The acetone washings were combined with the filtrate; the combined filtrate-washings were stripped. Acetone (about 200 ml) was added to the residue; the resulting mixture was allowed to sit overnight at room temperature. The mixture was filtered. The filtrate was stripped to give the crude product which was washed with hexane and ethyl ether, suction-filtered, and then air-dried to give the above-identified product as an off-white solid.

Elemental analysis for $C_7H_7ClN_2O$ showed: calculated %C 49.3, %H 4.14, and %N 16.4; found %C 51.37, %H 4.17, and %N 14.4.

Example 6

Preparation of O-Tricyclohexylstannyl-2-chlorobenzamidoxime-ether

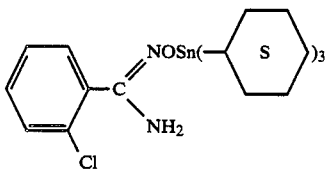

(a) To a stirred mixture of 2.1 g (0.012 moles) 2-chlorobenzamidoxime (the product of Example 5) in methanol (about 50 ml), 0.3 g (0.0128 moles) sodium metal was added slowly. The methanol was removed under reduced pressure in a hot water bath leaving the sodium salt of 2-chlorobenzamidoxime.

(b) The 2-chlorobenzamidoxime sodium salt from step (a) was stirred in 100 ml dimethoxyethane for 10 minutes; tricyclohexyl tin bromide, 5 g (0.0112 moles) was added all at once with stirring. The reaction mixture was refluxed about 10 hours. The dimethoxyethane was removed under reduced pressure and heat. Water (about 75 ml) and methylene chloride (about 125 ml) were added to the residue and the resulting mixture was stirred about 0.5 hours. The layers were phase-separated. The methylene chloride layer was washed with water, dried over magnesium sulfate, filtered and stripped to give about 5 g of the above-identified product as a thick liquid.

Elemental analysis for $C_{25}H_{39}ClN_2OSn$ showed: calculated %C 55.8, %H 7.31, and %N 5.21; found %C 55.34, %H 7.26, and %N 3.93.

Example 7

Preparation of (3,4-Dichlorothiophenoxy)acetonitrile

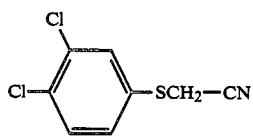

(a) To a mixture of 25 g (0.139 moles) 3,4-dichlorothiophenol in methanol which had been stirred for a few minutes at room temperature, 3.2 g (0.14 moles) sodium metal was added slowly and stirred until dissolved. Methanol was removed under reduced pressure and heat to give the sodium salt of 3,4-dichlorothiophenol.

(b) Dimethoxyethane (about 75 ml) was added to the sodium salt from step (a) and the resulting mixture was stirred. To that mixture, 11.9 g (0.1 moles) bromoacetonitrile in a small amount dimethoxyethane (about 5 ml) was dropped in slowly. The reaction mixture was refluxed about 16 hours. Dimethoxyethane was removed under reduced pressure and heat. Methylene chloride (about 75 ml) and water (about 125 ml) were added to the residue and the resulting mixture was stirred. The layers were phase separated. The methylene chloride layer was washed with water, dried over magnesium sulfate, filtered, and stripped to give the crude product. Chromatography on silica gel eluting with methylene chloride gave the above-identified product as a yellow liquid.

Elemental analysis for $C_8H_5Cl_2NS$ showed: calculated %C 44.1, %H 2.31, and %N 6.42; found %C 43.69, %H 2.46, and %N 6.98.

Example 8

Preparation of O-Tricyclohexylstannyl-3,4-dichlorothiophenylacetoamidoxime-ether

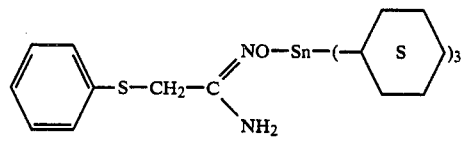

(a) To a stirred mixture of 3 g (0.01195 moles) 3,4-dichlorothiophenylacetoamidoxime in methanol (about 25 ml) which had been stirred for several minutes, 0.3 g (0.013 moles) sodium metal was aded slowly and stirred until dissolved. The mixture was stirred about 0.5 hour. The solvent, methanol, was stripped to give the sodium salt.

(b) Dimethoxyethane (about 75 ml) was added to the sodium salt from step (a) and the resulting mixture was stirred. Tricyclohexyl tin chloride, 4.8 g (0.01189 moles) was then added. The reaction mixture was refluxed for about 16 hours. The dimethoxyethane was removed by stripping. Water (about 75 ml) and methylene chloride (about 125 ml) were added to the residue. The layers were phase separated. The methylene chloride layer was washed twice with water, dried over magnesium sulfate, filtered and stripped to give the above-identified product, as a viscous amber liquid.

Elemental analysis for $C_{26}H_{40}Cl_2N_2OSSn$ showed: calculated %C 50.5, %H 6.52, and %N 4.53; found %C 50.93, %H 7.69, and %N 3.68

Example 9

Preparation of 4-Chlorobenzaloxime

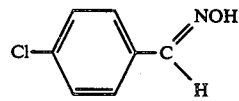

To a stirred mixture of 70.3 g (0.5 moles) 4-chlorobenzaldehyde and 40 g (0.58 moles) hydroxylamine hydrochloride in about 400 ml ethanol, about 46 g (1.16 moles) sodium hydroxide dissolved in 100 ml water were added dropwise. The reaction mixture was stirred at reflux for about 2 hours. The ethanol was removed under reduced pressure and heat. Isopropyl alcohol (about 100 ml) was added to the reaction mixture. The reaction mixture was stirred for about 2 hours, filtered, and stripped. The residue was washed in hexane and ethyl ether, filtered, air dried, and vacuum dried to give the above-identified product as a white solid, melting point 100°–102° C.

Elemental analysis for C₇H₆ClNO showed: calculated %C 54.0, %H 3.89, and %N 9.0; found %C 54.1, %H 4.03, and %N 7.98.

Example 10

Preparation of 4-Chlorobenzaloxime imidoyl chloride

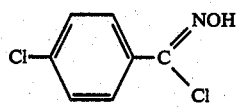

Into a mixture of 25 g (0.16 moles) 4-chlorobenzaloxime (the product of Example 9) in carbon tetrachloride cooled by an ice bath, chlorine gas was bubbled for about 3 hours; the solution turned a bluegreen color. The reaction mixture was stirred overnight; by morning the reaction mixture had turned an amber color. Nitrogen gas was bubbled through the reaction mixture to displace excess chlorine gas for about 1.5 hours. The reaction mixture was stirred overnight. The solvent was stripped under reduced pressure (using little or no heat) to give the above-identified product as an off-white, yellowish solid.

Example 11

Preparation of 4-Chloro-N,N-diethyl benzamidoxime

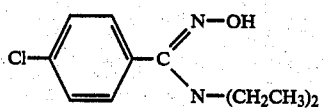

To a stirred mixture of 15 g (0.079 mole) 4-chlorobenzaloxime imodyl chloride (the product of Example 10) in the methylene chloride cooled with an ice bath, 11.6 g (0.159 mole) diethylamine was added slowly in several portions. The reaction mixture was allowed to come to room temperature and then was refluxed. The methylene chloride was removed under reduced pressure and heat. Water was added to the residue and the resulting mixture was stirred. The mixture was extracted with methylene chloride. The methylene chloride layer was washed twice with water (about 35 ml), dried over magnesium sulfate, filtered and stripped. The residue was washed with hexane and a small amount of ethyl ether, suction filtered to give about 2 g of the above-identified product as a light yellow solid.

Elemental analysis for C₁₁H₁₅ClN₂O showed: calculated %C 58.3, %H 6.67, and %N 12.4; found %C 56.84, %H 6.84, and %N 11.63.

Compounds prepared in accordance with Examples 1 to 11 are found in Table I.

In addition, by following the procedures described in the Detailed Description of the Invention and in Examples 1 to 11 and by using the appropriate starting materials, the following compounds are made:
O-tricyclohexylstannyl-4-chloro-N,N-diethylbenzamidoxime-ether;
O-tri-n-butylstannyl-4-chloro-N,N-diethylbenzamidoxime-ether;
(O-tricyclohexylstannyl)methylthio-N,N-diethylacetamidoxime-ether;
(O-tri-n-butylstannyl)methylthio-N,N-diethylacetamidoxime-ether;
O-tricyclohexylstannyl-3,4-dichlorothiophenyl-N,N-dimethyl-acetoamidoxime-ether;
O-tri-n-butyl-thiophenyl-N,N-dimethyl-acetoamidoxime-ether;
(O-tri-n-butylstannyl)methylthio-N-methylacetamidoxime-ether;
(O-triphenylstannyl)methylthio-acetamidoxime-ether;
O-triphenylstannyl-4-chloro-N,N-diethylbenzamidoxime-ether; and
O-triphenylstannyl-4-chloro-benzamidoxime-ether.

Example A

Bacterial Inhibition

Compounds of this invention were evaluated for in vitro bactericidal effectiveness by means of a bacterial inhibition test. This test is designed to measure the antibacterial activity of compounds in terms of degree of inhibition bacterial multiplication. The representative bacteria used were *Erwinia amylovora*, *Pseudomonas syringae* and *Xanthomonas vesicatoria*. Each compound to be tested was dissolved in acetone to give a 500 ppm concentration. Agar plates were inoculated using a micro sprayer with an suspension of the particular bacteria shortly (3 to 5 seconds) before treatment. The inoculated agar plates were then treated with the compound to be tested by spraying with a micro sprayer. The treated plates were incubated at 23.5° C. and the data was taken 24 hours after treatment. Antibacterial activities are measured by a zone of inhibited bacterial growth from the center of the agar plate and the deposit concentration in mg/cm² at the edge of the zone of inhibition (ED₉₉). The effectiveness of the compounds for antibacterial activity are reported in Table II in terms of the percent of the ED₉₉ of each compound of the ED₉₉ of the standard PMA (phenyl mercuric acetate).

Example B

Mycelial Inhibition

Compounds were evaluated for in vitro fungicidal effectiveness by means of a mycelial inhibition test. This test is designed to measure the fungitoxic activity of fungicidal chemicals in terms of their degree of inhibition of mycelium growth. Fungi used were *Pythium ultimum*, *Rhizoctonia solani*, *Fusarium moniloforme*, *Botrytis cinerea*, *Aspergillus niger* and *Ustilago hordeii*. Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a micro sprayer with the fungicidal solution. The treated paper strips were incubated at 25° C. and the data is taken after 24 hours. Fungicidal activities are measured by a zone of inhibited mycelial growth from the center of the paper strip in terms of mg/cm² needed for 99½ control of the fungus (ED₉₉). The effectiveness of the compounds for fungicidal activity are reported in Table III in terms of the percent of the ED₉₉ of the test compound of the ED₉₉ of the standard Difolatan ®.

Example C

Grape Downy Mildew

Compounds were tested for the control of the Grape Downy Mildew organism, *Plasmopara viticola*. Seedlings of *Vitis vinifera* var. Emperor (7+ weeks old) were used as hosts. The plants were sprayed with a 200 ppm solution of the test compound in an acetone and water solution containing a small amount of nonionic emulsifier. The treated plants were inoculated one day later by spraying them with a spore suspension of the organism. The treated plants were then held in a greenhouse at a temperature of about 68° F. to about 72° F. (relative humidify varied between about 30 and about 99%) for 4 days. The plants were then placed in an environmental chamber at 100% relative humidity to induce sporulation. On removal from the chamber and after drying, the plants were evaluated for disease development. The percent disease control provided by a given test compound was based on the percent disease reduction relative to untreated check plants. The results are reported in Table III.

Example D

Tomato Late Blight

Compounds were tested for the preventative control of the Tomato Late Blight organism *Phytophthora infestans*. Five- to six-week-old tomato (cultivar Bonny Best) seedlings were used. The tomato plants were sprayed with a 200-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table III.

Example E

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a non-ionic emulsifier (ORTHO X-77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 - 100 \times \left( \frac{\% \text{ disease in treated plants}}{\% \text{ disease in check}} \right)$$

The results are tabulated in Table III.

Example F

Tomato Early Blight

Compounds were tested for the control of the Tomato Early Blight organism *Alternaria solani*. Tomato (variety Bonny Best) seedlings of 6- to 7-weeks old were used. The tomato plants were sprayed with a 200-ppm solution of the test compound in an acetone-and-water solution containing a small amount of a nonionic emulsifier. The sprayed plants were inoculated 1 day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The results are tabulated in Table III.

Example G

Celery Late Blight

The Celery Late Blight tests were conducted using celery (Utah) plants 11 weeks old. The Celery Late Blight organism was *Septoria apii*. The celery plants were sprayed with 200-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given test compound is based on the percent disease reduction relative to untreated check plants. The results are reported in Table III.

Example H

Bean Powdery Mildew

Compounds were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results as percent control are tabulated in Table III.

Example I

Bean Rust

Compounds were evaluated for their ability to eradicate Bean Rust caused by *Uromyces phaseoli typica* on pinto beans.

Pinto bean plants, variety Idaho 1-11, 16 (summer) or 19 (winter) days old were inoculated with a 50-ppm suspension of uredospores in water containing a small amount of nonionic surfactant. The inoculated plants were placed in an environmental chamber immediately after inoculation and incubated 20 hours. Following the incubation period, the plants were removed from the chamber and placed in a greenhouse maintained at 66°-68° F. and 60-80% relative humidity. Two days after inoculation, the plants were treated by spraying with a 200-ppm solution of test compound in an acetone and water carrier formulation containing a small amount of nonionic surfactant. One or two replicate pots (each containing two plants) were used for each compound. In addition one or two replicate pots were sprayed with the same carrier formulation (without a test compound) as a control (hereinafter "untreated Checks"). The plants were kept in the greenhouse until evaluated. The plants were evaluated for disease control when disease symptoms were well developed on the untreated Checks, normally about 14 days after treatment. The percentage disease control (or eradication) provided by a test compound was based on the percent disease reduction relative to the untreated Checks. The results are reported in Table III.

Example J

Aphid Control

The compounds of this invention were tested for their insecticidal activity against cotton aphids (*Aphis gossypii* Glover). An acetone solution of the test compound containing a small amount of nonionic emulsifier was diluted with water to give a concentration of 40 ppm. Cucumber leaves infested with cotton aphids were dipped in the test compound solution. Mortality readings were taken after 24 hours. The results are tabulated in Table II in terms of percent control.

Example K

Aphid Systemic Evaluation

This procedure is used to assess the ability of a candidate insecticide to be absorbed through the plant root system and translocate to the foliage and thus to show insecticidal activity against the cotton aphid (*Aphis gossypii* Glover).

Two cucumber plants planted in a 4-inch fiber pot with a soil surface area of 80 cm$^2$ are used. Forty ml of an 80-ppm solution of the candidate insecticide is poured around the plants in each pot. (This corresponds to 40 gamma/cm$^2$ of actual toxicant.) The plants are maintained throughout in a greenhouse at 75°–85° F. Forty-eight hours after the drenching, the treated plants are infested with aphids by placing well-colonized leaves over the treated leaves so as to allow the aphids to migrate easily from the inoculated leaf to the treated leaf. Three days after infestation, mortality readings were taken. The results are tabulated in Table IV in terms of percent control.

Example L

Mite Adult

Compounds of this invention were tested for their insecticidal activity against parathion-resistant Two-spotted Spider Mite [*Tetranychus urticae* Koch]. An acetone solution of the candidate toxicant containing a small amount of nonionic emulsifier was diluted with water to 40 ppm. Lima bean leaves which were infested with mites were dipped in the toxicant solution. The results are tabulated in Table IV in terms of percent control.

Example M

Mite Egg Control

Compounds of this invention were tested for their ovicidal activity against eggs of the two-spotted spider mite [*Tetranychus urticae* Koch]. An acetone solution of the test toxicant containing a small amount of nonionic emulsifier was diluted with water to give a concentration of 40 ppm. Two days before testing, 2-week old lima bean plants were infested with spider mites. Two days after infestation, leaves from the infested plants are dipped in the toxicant solution, placed in a petridish with filter paper and allowed to dry in the open dish at room temperature. The treated leaves were then held in covered dishes at about 31° C. to 33° C. for seven days. On the eighth day egg mortality readings are taken. The results, expressed as percent control, are tabulated in Table IV.

Example N

Housefly

Compounds of this invention were tested for their insecticidal activity against the Housefly (*Musca domestica* Linnaeus). A 500-ppm acetone solution of the candidate toxicant was placed in a micro sprayer (atomizer). A random mixture of anesthetized male and female flies was placed in a container and 55 mg of the above-described acetone solution was sprayed on them. A lid was placed on the container. A mortality reading was made after 24 hours. The results are tabulated in Table IV in terms of percent control.

Example O

American Cockroach

Compounds of this invention were tested for their insecticidal activity against Chlorodoane-resistant American Cockroaches (*Periplaneta americana* Linnaeus). A 500-ppm acetone solution of the candidate toxicant was placed in a micro sprayer (atomizer). A random mixture of anesthetized male and female roaches was placed in a container and 55 mg of the above-described solution was sprayed on them. A lid was placed on the container. A mortality reading was made after 24 hours. The results are tabulated in Table IV in terms of percent control.

Example P

Alfalfa Weevil

The compounds of this invention were tested for their insecticidal activity against Alfalfa Weevil [*Hypera brunneipennis* (Boheman)]. A 500-ppm acetone solution of the candidate toxicant was placed in a micro sprayer (atomizer). A random mixture of male and female weevils was placed in a container and 55 mg of the above-described acetone solution was sprayed on them. A lid was placed on the container. A mortality reading was made after 24 hours. The results are tabulated in Table IV in terms of percent control.

Example Q

Cabbage Looper Control

The compounds of this invention were tested for their insecticidal activity against Cabbage Looper [*Trichoplusia ni* (Hubner)]. An acetone solution of the candidate toxicant containing a small amount of nonionic emulsifier was diluted with water to give a concentration of 500 ppm. Excised cucumber leaves were dipped in the toxicant solution and allowed to dry. The leaves were then infested with Cabbage Looper larvae. Mortality readings were taken after 24 hours. The results are tabulated in Table IV in terms of percent control.

TABLE I

Compounds of the Formula:

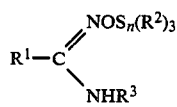

$$R^1-C\begin{matrix}\diagup NOS_n(R^2)_3 \\ \diagdown NHR^3\end{matrix}$$

| Compound | R¹ | R² | R³ | Physical State | %C Calc. | %C Found | %H Calc. | %H Found | %N Calc. | %N Found |
|---|---|---|---|---|---|---|---|---|---|---|
| 1 42699 | CH₃—S—CH₂ | —(CH₂)₃CH₃ | —H | Yellow liquid | 44.0 | 47.5 | 8.4 | 9.0 | 6.85 | 4.0 |
| 2 44181 | CH₃—S—CH₂— | (tetrahydrothiopyranyl) | —H | Pale amber semi-solid | 51.6 | 51.7 | 8.27 | 8.32 | 5.75 | 1.32 |
| 3 42752 | phenyl | —(CH₂)₃CH₂ | —H | Greenish liquid | 53.7 | 55.3 | 8.1 | 8.3 | 6.59 | 6.4 |
| 4 44458 | phenyl | (tetrahydrothiopyranyl) | —H | Yellow semi-solid | 59.9 | 61.6 | 7.64 | 8.13 | 5.59 | 4.35 |
| 5 43252 | 4-F-phenyl | —(CH₂)₃CH₃ | —H | Amber liquid | 53.2 | 51.5 | 7.75 | 7.51 | 6.52 | 6.32 |
| 6 44064 | 4-F-phenyl | (tetrahydrothiopyranyl) | —H | Greenish liquid | 57.6 | 54.8 | 7.54 | 8.06 | 5.38 | 4.88 |
| 7 44103 | 2-Cl-phenyl | (tetrahydrothiopyranyl) | —H | Yellow semi-solid | 55.8 | 55.3 | 7.31 | 7.26 | 5.21 | 3.93 |
| 8 43953 | 3-Br-phenyl | (tetrahydrothiopyranyl) | —H | Pale yellow semi-liquid | 51.6 | 54.2 | 6.75 | 7.42 | 4.81 | 2.43 |
| 9 42874 | 4-Cl-benzyl | —(CH₂)₃CH₃ | —H | Amber semi-solid | 50.7 | 51.5 | 7.5 | 7.6 | 5.91 | 6.62 |
| 10 45144 | 3,4-diCl-phenyl-S-CH₂— | (tetrahydrothiopyranyl) | —H | Viscous amber liquid | 50.5 | 50.93 | 6.52 | 7.69 | 4.53 | 3.68 |

TABLE II

| | Bacterial Inhibition | | |
|---|---|---|---|
| Compound | Pseudo | Erwin. | Xanth. |
| 1 42699 | 24 | 25 | 100 |
| 2 44181 | 0 | 0 | 0 |
| 3 42752 | 20 | 15 | 75 |
| 4 44458 | 0 | 0 | 0 |
| 5 43252 | 25 | 0 | 53 |
| 6 44064 | 0 | 0 | 0 |
| 7 44103 | 0 | 0 | 0 |
| 8 43953 | 0 | 0 | 0 |

TABLE II-continued

| Compound | Bacterial Inhibition | | |
|---|---|---|---|
| | Pseudo | Erwin. | Xanth. |
| 9 42874 | 0 | 0 | 100 |

Pseudo = *Pseudomonas syringae*
Erwin. = *Erwinia amylovora*
Xanth. = *Xanthomonas vesicatoria*

TBLE III

| | Fungicidal Activity | | | | | | | | | | | |
|---|---|---|---|---|---|---|---|---|---|---|---|---|
| | Mycelial Inhibition | | | | | | | | | | | |
| Compound | Pyth. | Rhiz. | Fusar. | Botry. | Asper. | Ustil. | GDM | TLB | RB | TEB | CLB | BPM | Br |
| 1 42699 | 38 | 36 | 60 | 80 | 45 | 0 | 67 | 93 | 96 | — | 93 | 36 | 0 |
| 2 44181 | 0 | 0 | 0 | 0 | 0 | 0 | — | 63 | 0 | 7 | 95 | 100 | 0 |
| 3 42752 | 13 | 51 | 55 | 37 | 50 | 0 | 0 | 92 | 0 | 0 | 92 | 23 | 0 |
| 4 44458 | 0 | 0 | 0 | 0 | 0 | 0 | — | 88 | 21 | 80 | 100 | 75 | 0 |
| 5 43252 | 48 | 33 | 61 | 39 | 75 | — | — | 69 | 50 | 0 | — | 31 | 25 |
| 6 440624 | 0 | 0 | 0 | 0 | 0 | 26 | — | 91 | 0 | 0 | 81 | 97 | 0 |
| 7 44103 | 0 | 0 | 69 | 0 | 0 | 50 | — | 91 | — | 0 | 75 | 97 | 0 |
| 8 43953 | 0 | 0 | 0 | 0 | 0 | 51 | — | 91 | 0 | 21 | 92 | 100 | 0 |
| 9 42874 | 34 | 65 | 83 | 15 | 114 | — | — | 55 | 72 | 0 | 67 | 0 | 0 |

— = No results available (Not tested or test failed)
Pyth. = *Pythium ultimum*
Rhiz. = *Rhizoctonia solani*
Fusar. = *Fusarium moniloforme*
Botry. = *Botrytis cinerea*
Asper. = *Aspergillus niger*
Ustil. = *Ustilago hordeii*
GDM = Grape Downy Mildew
TLB = Tomato Late Blight
RB = Rice Blast
TEB = Tomato Early Blight
CLB = Celery Late Blight
BPM = Bean Powdery Mildew
BR = Bean Rust

TABLE IV

| | Insecticidal and Miticidal Activity | | | | | | | | |
|---|---|---|---|---|---|---|---|---|---|
| Compound | AR | AW | HF | MA | ME | Aph. | AS | CL | 5-CL |
| 1 42699 | 70 | 0 | 95 | 95 | 0 | 0 | 0 | 12 | 70 |
| 2 44181 | 0 | 0 | 0 | 70 | 100 | 0 | 0 | 0 | 0 |
| 3 42752 | 0 | — | 50 | 80 | 100 | 100 | 0 | 40 | 100 |
| 4 44458 | 0 | 0 | 0 | 75 | 80 | 0 | 0 | 0 | 50 |
| 5 43252 | 60 | 0 | — | 100 | 100 | 0 | 0 | 100 | 100 |
| 6 44064 | 0 | 0 | 0 | 100 | 100 | 0 | 0 | 0[1] | 0 |
| 7 44103 | 0 | 40 | 0 | 90 | 90 | 0 | 0 | 0 | 0 |
| 8 43953 | 0 | 0 | 0 | 50 | 100 | 0 | 0 | 20[1] | 0 |
| 9 42874 | 20 | — | 0 | 100 | 0 | 40 | 0 | 0 | 80 |

[1] Feeding reduced.
AR = American Cockroach
AW = Alfalfa Weevil
HF = Housefly
MA = Mite Adult
ME = Mite Egg
Aph. = Aphid
AS = Aphid Systemic
CL = Cabbage Looper
5-CL = 5-Day Reading of Cabbage Looper Mortality

What is claimed is:

1. A compound of the formula:

$$R^1C\underset{NR^3\!-\!R^4}{\overset{NOSn(R^2)_3}{\diagup\!\!\!\!\diagdown}}$$

wherein $R^1$ is lower alkyl of 1 to 6 carbon atoms; alkylthioalkylene of 2 to 5 carbon atoms; aryl of 6 to 10 carbon atoms; aralkyl of 7 to 12 carbon atoms; arylthioalkyl of 7 to 11 carbon atoms; or substituted aryl, substituted aralkyl or substituted arylthioalkyl each substituted with 1 to 3 substitutents independently selected from halo, nitro, lower alkoxy of 1 to 4 carbon atoms, or lower alkyl of 1 to 4 carbon atoms; $R^2$ is lower alkyl of 1 to 6 carbon atoms, lower cycloalkyl of 3 to 8 carbon atoms, phenyl or benzyl; and $R^3$ and $R^4$ are independently hydrogen, lower alkyl of 1 to 6 carbon atoms or phenyl.

2. A compound according to claim 1 wherein $R^1$ is alkylthioalkylene.

3. A compound according to claim 2 wherein $R^3$ is hydrogen.

4. A compound according to claim 3 wherein $R^1$ is methylthiomethylene.

5. A compound according to claim 4 wherein $R^2$ is n-butyl.

6. A compound according to claim 4 wherein $R^2$ is cyclohexyl.

7. A compound according to claim 1 wherein $R^1$ is aryl or substituted aryl.

8. A compound according to claim 7 wherein $R^3$ is hydrogen.

9. A compound according to claim 8 wherein $R^1$ is phenyl or phenyl substituted with one halogen atom.

10. A compound according to claim 9 wherein said halogen atom is in the para position.

11. A compound according to claim 10 wherein $R^1$ is phenyl.

12. A compound according to claim 11 wherein $R^2$ is n-butyl.

13. A compound according to claim 10 wherein $R^1$ is para-halo-phenyl.

14. A compound according to claim 13 wherein $R^2$ is n-butyl or cyclohexyl.

15. A compound according to claim 14 wherein $R^1$ is para-bromophenyl and $R^2$ is cyclohexyl.

16. A compound according to claim 1 wherein $R^1$ is arylthioalkylene or substituted arylthioalkylene.

17. A method of controlling fungi which comprises contacting said fungi or their growth environment with a fungicidally effective amount of a compound of claim 1.

18. A method of controlling fungi which comprises contacting said fungi or their growth environment with a fungicidally effective amount of a compound of claim 2.

19. A method of controlling fungi which comprises contacting said fungi or their growth environment with a fungicidally effective amount of a compound of claim 4.

20. A method of controlling fungi which comprises contacting said fungi or their growth environment with a fungicidally effective amount of a compound of claim 5.

21. A method of controlling fungi which comprises contacting said fungi or their growth environment with a fungicidally effective amount of a compound of claim 7.

22. A method of controlling fungi which comprises contacting said fungi or their growth environment with a fungicidally effective amount of a compound of claim 16.

23. A fungicidal composition which comprises an inert carrier and a fungicidally effective amount of a compound of claim 1.

24. A fungicidal composition which comprises an inert carrier and a fungicidally effective amount of a compound of claim 2.

25. A fungicidal composition which comprises an inert carrier and a fungicidally effective amount of a compound of claim 4.

26. A fungicidal composition which comprises an inert carrier and a fungicidally effective amount of a compound of claim 5.

27. A fungicidal composition which comprises an inert carrier and a fungicidally effective amount of a compound of claim 7.

28. A fungicidal composition which comprises an inert carrier and a fungicidally effective amount of a compound of claim 16.

* * * * *